(12) United States Patent
Owens et al.

(10) Patent No.: US 10,850,008 B2
(45) Date of Patent: Dec. 1, 2020

(54) METHODS AND SYSTEMS FOR STIFFENING OF TISSUE FOR IMPROVED PROCESSING

(71) Applicant: LifeCell Corporation, Branchburg, NJ (US)

(72) Inventors: Rick T. Owens, Stewartsville, NJ (US); Gregory Christopherson, Bridgewater, NJ (US)

(73) Assignee: LifeCell Corporation, Madison, NJ (US)

( * ) Notice: Subject to any disclaimer, the term of this patent is extended or adjusted under 35 U.S.C. 154(b) by 1027 days.

(21) Appl. No.: 15/374,395

(22) Filed: Dec. 9, 2016

(65) Prior Publication Data

US 2017/0165402 A1 Jun. 15, 2017

Related U.S. Application Data

(60) Provisional application No. 62/266,221, filed on Dec. 11, 2015.

(51) Int. Cl.
*A61L 27/36* (2006.01)
*A61L 27/60* (2006.01)
(Continued)

(52) U.S. Cl.
CPC ....... *A61L 27/3691* (2013.01); *A61L 26/0033* (2013.01); *A61L 26/0057* (2013.01);
(Continued)

(58) Field of Classification Search
CPC .. A61L 27/3691; A61L 31/005; A61L 31/044; A61L 26/0033; A61L 26/0057;
(Continued)

(56) References Cited

U.S. PATENT DOCUMENTS

| 2,836,181 A | 5/1958 | Tapp |
| 3,157,524 A | 11/1964 | Artandi |

(Continued)

FOREIGN PATENT DOCUMENTS

| EP | 1153622 A1 | 11/2001 |
| WO | 1998/40112 A1 | 9/1998 |

(Continued)

OTHER PUBLICATIONS

Khiari, Zied, et al. "Low Molecular Weight Bioactive Peptides Derived from the Enzymatic Hydrolysis of Collagen after Isoelectric Solubilization/Precipitation Process of Turkey by-Products." Poultry Science, vol. 93, No. 9, 2014, pp. 2347-2362., doi:10.3382/ps.2014-03953. (Year: 2014).*

(Continued)

*Primary Examiner* — David H Willse
*Assistant Examiner* — Javier G Blanco
(74) *Attorney, Agent, or Firm* — McCarter & English, LLP; Matthew R. Van Eman

(57) ABSTRACT

Methods and systems for stiffening of tissue are presented to allow improved processing. Solutions including an acid or a base can be contacted with tissue to stiffen one or more components of the tissue. The resulting stiffened tissue can be used in the creation of wound treatment devices.

20 Claims, 7 Drawing Sheets

(51) Int. Cl.
*A61L 26/00* (2006.01)
*A61L 31/04* (2006.01)
*A61L 31/00* (2006.01)
*A61L 27/24* (2006.01)

(52) U.S. Cl.
CPC ............ *A61L 27/24* (2013.01); *A61L 27/362* (2013.01); *A61L 27/3687* (2013.01); *A61L 27/60* (2013.01); *A61L 31/005* (2013.01); *A61L 31/044* (2013.01); *A61L 2430/34* (2013.01); *A61L 2430/40* (2013.01)

(58) Field of Classification Search
CPC .... A61L 27/60; A61L 27/3687; A61L 27/362; A61L 27/02; A61L 2430/40; A61L 2430/34
See application file for complete search history.

(56) References Cited

U.S. PATENT DOCUMENTS

| | | | |
|---|---|---|---|
| 5,284,655 | A | 2/1994 | Bogdansky et al. |
| 5,336,616 | A | 8/1994 | Livesey et al. |
| 5,364,756 | A | 11/1994 | Livesey et al. |
| 5,418,222 | A | 5/1995 | Song et al. |
| 5,460,962 | A | 10/1995 | Kemp |
| 5,993,844 | A | 11/1999 | Abraham et al. |
| 6,152,142 | A * | 11/2000 | Tseng ............... A01N 1/02 128/898 |
| 6,381,026 | B1 | 4/2002 | Schiff et al. |
| 6,933,326 | B1 | 8/2005 | Griffey et al. |
| 7,186,557 | B2 | 3/2007 | Marko |
| 7,326,571 | B2 | 2/2008 | Freyman |
| 7,358,284 | B2 | 4/2008 | Griffey et al. |
| 7,476,398 | B1 | 1/2009 | Doillon et al. |
| 7,498,412 | B2 | 3/2009 | Huang et al. |
| 7,767,114 | B2 | 8/2010 | Gordon et al. |
| 8,198,408 | B2 | 6/2012 | Huang |
| 9,382,422 | B2 | 7/2016 | Owens et al. |
| 9,526,484 | B2 | 12/2016 | Armstrong |
| 2003/0035843 | A1 | 2/2003 | Livesey et al. |
| 2003/0143207 | A1 | 7/2003 | Livesey et al. |
| 2003/0225355 | A1 | 12/2003 | Butler |
| 2004/0029478 | A1 | 2/2004 | Planck et al. |
| 2004/0253718 | A1 | 12/2004 | Marko |
| 2005/0013872 | A1 | 1/2005 | Freyman |
| 2005/0028228 | A1 | 2/2005 | McQuillan et al. |
| 2005/0159776 | A1 | 7/2005 | Armstrong |
| 2006/0073592 | A1 | 4/2006 | Sun et al. |
| 2006/0127375 | A1 | 6/2006 | Livesey et al. |
| 2006/0149040 | A1 | 7/2006 | Snowden |
| 2006/0153815 | A1 | 7/2006 | Seyda et al. |
| 2006/0177513 | A1 | 8/2006 | Martin et al. |
| 2006/0210960 | A1 | 9/2006 | Livesey et al. |
| 2007/0014729 | A1 | 1/2007 | Farhat et al. |
| 2007/0202189 | A1 | 8/2007 | Ahlfors |
| 2007/0248575 | A1 | 10/2007 | Connor et al. |
| 2008/0281434 | A1 | 11/2008 | Schmidt et al. |
| 2009/0192528 | A1 | 7/2009 | Higgins et al. |
| 2010/0256774 | A1 | 10/2010 | Wang et al. |
| 2012/0053690 | A1 | 3/2012 | Frank |
| 2012/0276203 | A1 | 11/2012 | Selim et al. |
| 2013/0190893 | A1 | 7/2013 | Roock et al. |
| 2013/0302435 | A1* | 11/2013 | Pedroso ............ A61L 27/3662 424/548 |
| 2014/0377833 | A1 | 12/2014 | Chen et al. |
| 2016/0317707 | A1 | 11/2016 | Owens et al. |

FOREIGN PATENT DOCUMENTS

| | | |
|---|---|---|
| WO | 2000/016822 A1 | 3/2000 |
| WO | 2003/032735 A1 | 4/2003 |
| WO | 2003/084410 A1 | 10/2003 |
| WO | 2007/124302 A2 | 11/2007 |
| WO | 2009/009620 A2 | 1/2009 |
| WO | 2012/050836 A1 | 4/2012 |

OTHER PUBLICATIONS

Butler et al. "Reduction of Adhesions with Composite AlloDerm/Propylene Mesh Implants for Abdominal Wall Reconstruction", Plastic and Reconstructive Surgery, 114(2):464-473. (Apr. 24, 2003).
Chaplin et al.; "Use of an Acellular Dermal Allograft for Dural Replacement: An Experimental Study"; Neurosurgery; 45(2):320-327 (Apr. 7, 1999).
International Search Report and Written Opinion for International Patent Application No. PCT/US2008/069563; dated Jan. 9, 2009.
Kessler et al.; "Chromatographic Fractionation of Acetic Acid-solubilied Rat Tail Tendon Collagen;" J. Bio. Chem., 235(4):989-994 (Jun. 25, 1959).
Liang et al., "Alpha 1,3-galactoslytransferase knowckout does not alter the properties of porcine extracellular matrix bioscaffolds", Ada Biomat, 7:1719-1727 (Jan. 3, 2011).
Tedder et al.; "Stabilized Collagen Scaffols for Heart Valve Tissue Engineering"; Tissue Engineering: Part A; 1-12 (Aug. 25, 2008).
International Search Report and Written Opinion for Application No. PCT/US2016/065864, dated Aug. 16, 2017. 15 pages.

* cited by examiner

METHODS AND SYSTEMS FOR STIFFENING OF TISSUE FOR IMPROVED PROCESSING

This application claims the benefit of the filing date under 35 U.S.C. § 119(e), of U.S. Provisional Application No. 62/266,221, filed on Dec. 11, 2015, the entire contents of which is herein incorporated in its entirety by reference.

The present disclosure relates generally to devices and methods for treating wounds and, in particular, to devices and methods for treating deep or tunneling wounds including fistulas.

Deep wounds including fistulas and tunneling wounds can be challenging to treat and may require use of specialized fillers or plugs including synthetic plugs and injectable, collagen-based materials. Synthetic devices, although effective, do not regenerate natural tissue and may require relatively long-term presence of a foreign body, while injectable materials may become prematurely resorbed or may migrate from the target treatment site.

Although a number of acellular tissue matrix products are currently available, machining or processing those materials to produce new shapes can be challenging. For example, such tissues are often soft and flexible—making cutting, shearing, drilling, or otherwise machining difficult. Thus, improved methods of tissue preparation and processing are needed.

Accordingly, the present disclosure provides methods for altering tissue matrix products to facilitate processing and machining. The methods can be used to produce devices that are tailored to a variety of shapes and sizes to completely fill a wound or fistula space. The methods can further or alternatively provide means for producing devices that are more uniform, higher quality, and/or have improved biologic responses when implanted in vivo. The improved devices and methods can allow treatment of deep, tunneling wounds, and/or fistulas.

A method of producing a wound treatment device is presented in accordance with various embodiments. The method can include selecting a tissue and contacting the tissue with a solution comprising an acid or a base at a concentration selected to produce a desired level of stiffening of one or more components in the tissue. In some embodiments, the solution does not cause substantial irreversible denaturation of the one or more components in the tissue. The method also includes machining the stiffened tissue to produce a desired size and shape.

A wound treatment device produced by a process is presented in accordance with various embodiments of the present invention. The process of producing the wound treatment device can include selecting a tissue and contacting the tissue with a solution comprising an acid or a base at a concentration selected to produce a desired level of stiffening of one or more components in the tissue. In some embodiments, the solution does not cause substantial irreversible denaturation of the one or more components in the tissue. The process of producing the wound treatment device also includes machining the stiffened tissue to produce the wound treatment device having a desired configuration.

A method of producing a wound treatment device is presented in accordance with various embodiments of the present invention. The method can comprise selecting a tissue; contacting the tissue with a fluid comprising an acid or a base at a concentration selected to produce a desired level of stiffening of one or more components in the tissue; machining the stiffened tissue to produce a desired size and shape; and treating the tissue with an enzyme.

A device for treating a fistula is presented in accordance with various embodiments of the present invention. The device can comprise an elongated tissue matrix composition, wherein the tissue matrix composition comprises an acellular tissue matrix that is formed from a tissue that has been treated with an acid to stiffen the tissue and has been treated with a protease to remove immunogenic materials from the tissue matrix.

Also provided are methods of treatment including implantation of the disclosed devices in or on a treatment site.

DESCRIPTION OF EXEMPLARY EMBODIMENTS

Figure 1:
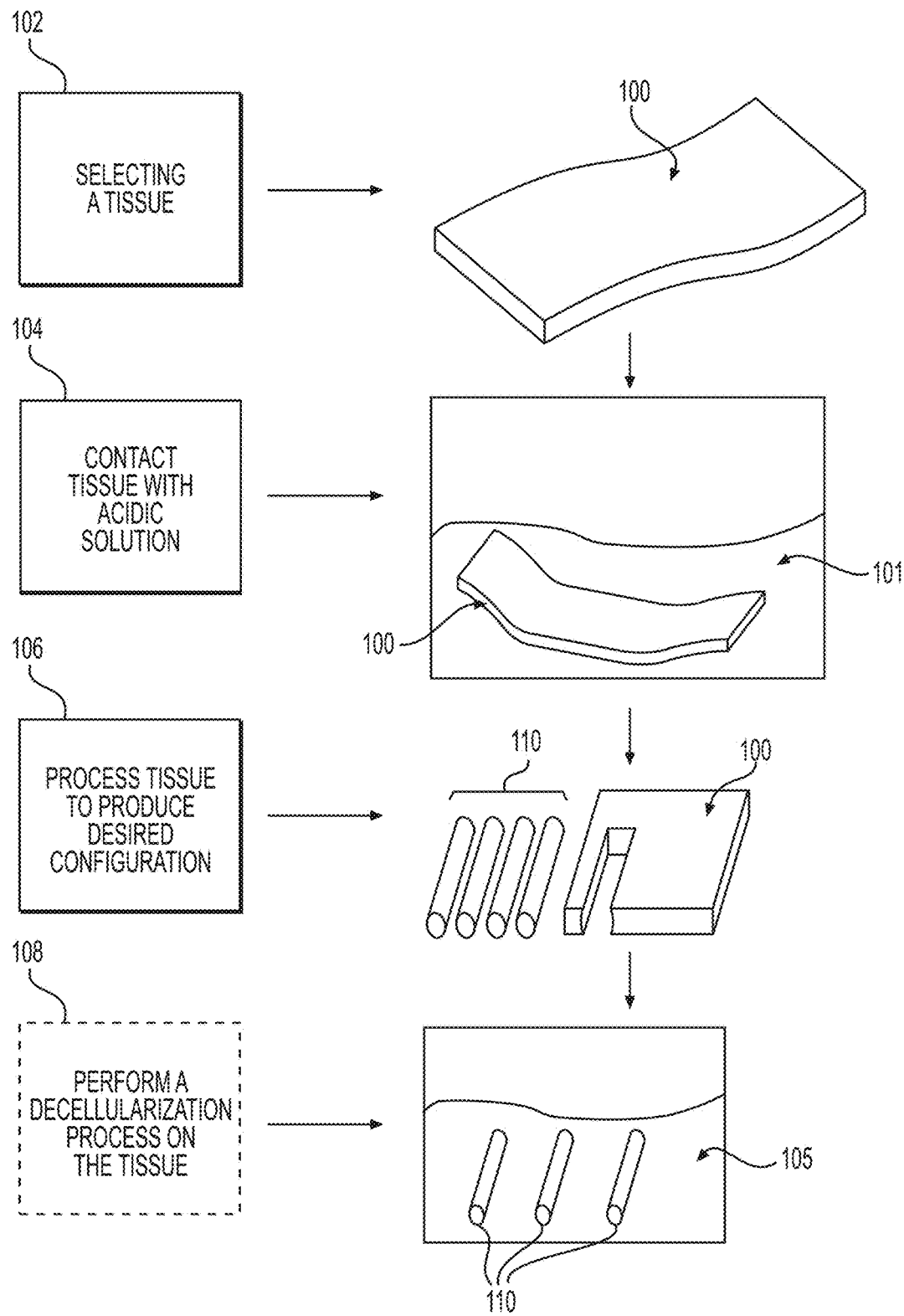
FIG. 1 depicts a process for producing a tissue product according to various embodiments.

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various tissue products are available for treatment of hard and/or soft tissues. Such tissue products can include processed tissues that have been treated to remove some or all of the cellular components and/or other materials (e.g., antigens and lipids). Such tissue products can be used for treatment, repair, regeneration, and/or augmentation of a variety of different tissues. For example, acellular tissue matrices can be used to replace soft tissue lost or damaged due to, for example, surgery, trauma, disease, and/or atrophy.

Current tissue matrices or other tissue scaffold or replacement materials (e.g., processed collagen or synthetic materials) are available in a variety of different forms. For example, STRATTICE™ and ALLODERM® (LIFECELL® Corporation, Branchburg, N.J.) are two acellular dermal tissue matrix products that are sold as sheets. In addition, CYMETRA® (also from LIFECELL®) is a dry, particulate acellular dermal matrix that is produced by cryofracturing acellular dermis. Each of these materials can be used to treat various anatomic sites. STRATTICE™ and ALLODERM® can be used for soft tissue augmentation, e.g., to treat abdominal wall defects; and CYMETRA® can be injected for soft tissue augmentation.

Although currently available tissue matrices are suitable for treatment of certain anatomic sites, such materials may not be well-suited for some applications. For example, deep wounds require a tissue matrix that is long enough to fill the entire wound without leaving gaps or unfilled areas. Production of appropriately dimensioned and shaped tissue matrices (with lengths on the order of several centimeters or more, while perhaps including a narrow width) can be challenging because the precursor tissue is often flexible or pliable and does not lend itself readily to machining, cutting, shearing, drilling, or other tooling techniques. Accordingly, the present disclosure provides a method of treating a tissue to stiffen the tissue prior to machining or cutting. The resulting tissue products produced by the methods described herein can be used to fill tissue defects having deep, variable, and/or irregular geometries. In addition, the tissue products of the present disclosure can provide suitable configurations to allow cellular ingrowth and vascular formation.

The present disclosure relates generally to devices and methods for stiffening tissues or tissue matrices. The resulting stiffened tissues or tissue matrices can be further processed to form wound treatment devices for treating deep or tunneling wounds. Such wounds can include, for example, tunneling wounds that form on the skin (e.g., on the limbs), and can extend through subcutaneous tissues, e.g., through fascia, muscle, and/or into bone. Such wounds can be associated with trauma, surgery, infection, and/or a variety of different diseases (e.g., vascular disorders and/or diabetes). In addition, for purposes of the present application, deep or tunneling "wounds" will be understood to include fistulas or other anatomic/structural malformations, including anal fistulas, recto-vaginal fistulas, recto-anal fistulas, fistulas relating to urinary structures, and any other abnormal anatomic openings or spaces that would desirably be closed by surgical or nonsurgical means.

The devices and methods described herein can include or allow production of a stiffened tissue or tissue matrix that can better tolerate machining and manipulation techniques designed to form wound treatment devices. The resulting wound treatment devices can provide a number of improvements over existing materials used to repair or otherwise treat tunneling wounds and fistulas. For example, the devices described herein can be formed of regenerative materials, e.g., regenerative acellular tissue matrices that support the ingrowth of surrounding cells and regeneration of tissue. In some cases, the materials are selected to allow formation of tissue that is similar to naturally occurring tissue and has limited or no scar formation.

Methods and devices described herein can better tailor the size and shape of a resulting wound treatment device to a particular wound. For example, the devices described herein can include stiffened tissue that is configured such that can be easily tailored to the desired the shape and size, including the length, width, and curvature of a resulting wound treatment device to completely or nearly completely fill a wound, including filling of long or tortuous wounds, such as fistulas.

FIG. 1 illustrates a process for producing a wound treatment device according to various embodiments. As shown at step 102, the process begins with selecting a tissue 100. Suitable tissues can include any human or animal tissue that can be formed into a substantially acellular tissue matrix that retains the ability to support cellular ingrowth and tissue regeneration without excessive inflammation. For example, suitable tissues include but are not limited to dermal tissue, adipose tissue, transitional dermal tissue, fascia, pericardial tissue, dura, umbilical cord tissue, cartilage, tendon, reticulate, placental tissue, cardiac valve tissue, ligament tissue, tendon tissue, arterial tissue, venous tissue, neural connective tissue, urinary bladder tissue, ureter tissue, small-intestine submucosa, or other tissues containing a high content of collagen. The source of the tissue may be human or non-human mammals such as, for example but not limited to, pigs. The suitable tissue can include intact tissues or tissues that have been partially decellularized or populated with exogenous cells.

Next, as shown in step 104, the tissue 100 is processed by immersion in or otherwise contacting the tissue with a solution 101. Immersion of the tissue 100 can include total immersion wherein the entire tissue is submerged in the solution 101 or partial immersion wherein only a portion of the tissue is submerged. In addition, the solution may be sprayed or otherwise applied to the tissue as long as a sufficient amount the solution contacts the tissue to produce the desired stiffening. It should be noted that the "solution" may not include 100% dissolved components, but generally would be understood to include a fluid in which the tissue can be immersed.

The solution 101 may include acidic or basic components. Acidic components of the solution 101 can include but are not limited to hydrochloric, sulfuric, carbonic, hydrofluoric, nitric, oxalic, phosphoric, boric, citric, malic, ascorbic, lactic, formic, or any other acid that meets application-specific requirements. In an exemplary embodiment, the solution 101 includes acetic acid. Basic components of the solution 101 can include but are not limited to lye, sodium hydroxide, potassium hydroxide, or any other base that meets application-specific requirements. The molar strength of the acidic or base can be chosen to meet the needs of an application. In an exemplary embodiment, the molarity of an acidic or basic component of a solution is 0.1 M, but it will be understood that the concentration may be selected based on the acid(s) used and the desired pH. In accordance with various embodiments, the molar strength and chemical composition of the solution 101 can be chosen to avoid substantial irreversible denaturation of one or more components in the tissue. In one embodiment, the solution 101 does not cause substantial irreversible denaturation of collagen fibers. In some embodiments, the pH of the solution 101 is in a range between 2 and 3.5, between 1 and 4, between, 2 and 3, between 2.5 and 4. In some cases, the pH is not less than 1, not less than 1.5, not less than 2.

Substantial irreversible denaturization can be understood to refer to denaturization that results in undesired biologic properties, such us reduced cellular infiltration or excess inflammation. In addition, denaturization can be measured by excessive shift in onset denaturization temperatures of differential scanning caliorimetry (e.g., a shift great than 5 degrees Celsius).

The tissue 100 can be immersed in the solution 101 for durations and temperatures as required by other system constraints and/or desired tissue properties. In some embodiments, the tissue 100 is immersed in the solution 101 for between about of 2 to 48 hours, 2 to 72 hours, between 2 and 24 hours, less than 48 hours, and less than 24 hours. In various embodiments, the tissue 100 immersed in the solution 101 is held at room temperature, or at cooled temperature (e.g., cooled but not frozen). In accordance with various embodiments, the tissue 100 can be de-fatted before being immersed in the solution 101. In some embodiments, for skin, "de-fatting" may include removal of a subcutaneous fat layer while maintaining dermal and/or epidermal layer.

Tissue 100 that is immersed in the solution 101 may experience a variable degree of swelling depending on structural properties of the tissue 100. Structural properties include, but are not limited to, collagen density and fat intercalation. In some embodiments, firm regions of a tissue 100 may swell to a lesser degree than pliable regions. The increased swelling of pliable regions of the tissue 100 may lead to a mechanically weaker region of tissue 100 that can be difficult to tool depending upon the application. Thus, concomitant swelling of a tissue 100 that may occur when immersed in a solution 101 is not as advantageous as the change in stiffness properties of the tissue 100. In some embodiments, the resulting stiffened tissue 100 may have a Young's modulus value in the range of 100 to 3000 MPa. The stiffened tissue 100 may bend under force but can have a level of elasticity that causes the shape to slowly restore.

Next, as shown at step 106, the stiffened tissue 100 is machined to produce one or more wound treatment devices 110. The machining or tooling process can include, but is not limited to, drilling, coring, cutting, slicing, machining, punching, dicing, or any other tooling technique that meets application-specific requirements. The tissue 100 can be divided into smaller pieces before machining. In some embodiments, the tissue 100 can initially be cut into section (e.g., 10×10 cm sections or other appropriate sizes depending on the source tissue and scale of production) in preparation for further machining. The stiffened tissue 100 can be mounted in a fashion that enhances machinability such as in a jig. In addition, the machining process can proceed along any directional axis of the tissue 100 or in any orientation. In an exemplary embodiment, the stiffened tissue 100 can be cored using a hollow drill bit along an axis parallel to the surface of the tissue 100 (i.e., a transverse axis). If the stiffened tissue 100 is dermal tissue, the tissue 100 can be machined along an axis parallel to the dermal-epidermal interface, or analogous direction if the epidermis has been removed. The machining or tooling process can be entirely manual or can include automated steps such as the use of a Computer Numerical Control (CNC)-enabled machine. If the machining process utilizes a drill or other rotating element, the process may use more than one rotation speed for the rotating element to optimize shape, texture, or any other feature of the resulting wound treatment device 110.

The wound treatment device(s) 110 can be created in a range of sizes and shapes. As a non-limiting example, the wound treatment devices 110 can be cylindrical or cylindrical-like having a substantially circular or oval cross-section and a length. It will be under stood that cylindrical and cylindrical-like will be understood to refer to any shape resembling a cylinder, but not necessarily meeting the mathematical definition of a cylinder. Such a device can be generally elongated tube like structure and need not be perfectly symmetric in cross-section. In some embodiments, the cylinder can have a width (or for circular devices, a diameter of the circular cross-section) in a range of 1 to 5 mm, 1 mm to 1 cm, 1 mm to 2 cm. In certain embodiments, at least one of the dimensions of a wound treatment device can be greater than 1 centimeter, greater than 3 centimeters, or greater than 5 centimeters in length, between 1 and 20 cm, 1 and 10 cm, 5 and 15 cm, 2 and 15, cm, or 2 and 10 cm. In some embodiments, a wound treatment device 110 can have a substantially spherical, ovoid, cubic, or other three-dimensional polygonal shape. In some embodiments, the wound treatment device 110 as-machined can have a Young's modulus value in the range of 100 and 3,000 MPa.

For some tissues, differences in fat intercalation of the tissue and changes in collagen density can contribute to curling or folding of stiffened tissue. In accordance with various embodiments, a tissue 100 undergoing a stiffening procedure may be mechanically restrained to cause the resulting stiffened tissue to lay substantially flat. In other embodiments, a jig or the machining device itself may be adapted to handle tissue that is curved or bulged. In some embodiments, the solution 101 can be applied at different strengths or for different lengths of time to portions of a tissue 100 to cause the resulting stiffened tissue to lay substantially flat.

After the wound treatment devices 110 have been created, one or more post-processing steps can be applied to them. The wound treatment device 110 can undergo one or more washing steps to remove remnants of the solution 101. Washing steps can include placing the wound treatment device(s) 110 in contact with water, buffer solutions or washes such as phosphate-buffered saline (PBS), or any other suitable washing solution. In accordance with various embodiments, washing the wound treatment device 110 or stiffened tissue 100 can reverse the effects of the solution 101 and return the tissue 100 to a substantially similar state as that before the immersion began (other than the machined shape changes). That is, washing the wound treatment device 110 or stiffened tissue 100 can cause loss of stiffness and partially or completely revert the tissue 100 back to its original pliability. In some embodiments, the washed wound treatment device 110 can have a Young's modulus value in the range of 0.1 and 1 MPa. In addition, the washing step(s) may reduce or reverse any swelling of the tissue that may have occurring. A washed wound treatment device 110 can be soft and/or pliable enough to be easily bent in half such that the ends touch.

In some optional embodiments, the wound treatment device 110 or tissue 100 can be subjected to a decellularization technique to create a substantially acellular tissue matrix as shown in step 108 of FIG. 1. In step 108, the tissue 100 or wound treatment device 110 is placed in contact with a decellularization solution 105 or otherwise treated to remove cellular components. In accordance with various embodiments, decellularization of the tissue 100 can occur before the tissue undergoes an acid-stiffening treatment and is machined to shape. In other embodiments, the wound treatment device(s) 110 that result from the stiffening and machining process can further be subjected to the decellularization treatment.

In general, the steps involved in the production of an acellular tissue matrix include removal of cells from donor tissue (e.g., a human cadaver or animal source) under conditions that preserve biological and structural function. In certain embodiments, the process includes chemical treatment to stabilize the tissue 100 or wound treatment device 110 and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue 100 or wound treatment device 110 is then placed in a decellularization solution 105 to remove viable cells (e.g., epithelial cells, endothelial cells, smooth muscle cells, and fibroblasts) from the structural matrix without damaging the biological and structural integrity of the collagen matrix. The decellularization solution 105 may contain an appropriate buffer, salt, an antibiotic, one or more detergents, one or more agents to prevent cross-linking, one or more protease inhibitors, and/or one or more enzymes. In some embodiments, the decellularization solution 105 comprises a detergent or enzymes, or both In some embodiments, the tissue 100 or wound treatment device 110 is incubated in the decellularization solution 105 overnight at 37° C. In certain embodiments, additional detergents may be used to remove fat from the tissue sample. Alternatively, instead of using or in addition to use of detergents, other decellularization processes can be used, including, for example, treatment with acids, enzymes, or other processes.

After the decellularization process, the tissue 100 or wound treatment device 110 is washed thoroughly with saline. In some exemplary embodiments, e.g., when xenogenic material is used, the decellularized tissue is then treated overnight at room temperature with a deoxyribonuclease (DNase) solution.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response of the recipient against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id.

Since non-primate mammals (e.g., pigs) produce α-gal epitopes, xenotransplantation of collagen-containing material from these mammals into primates often results in rejection because of primate anti-gal binding to these epitopes on the collagen-containing material. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue 100 or wound treatment device 110 thoroughly with saline, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. Any suitable enzyme concentration and buffer can be used as long as sufficient removal of antigens is achieved.

Alternatively, rather than treating the tissue 100 or wound treatment device 110 with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals, see U.S. application Ser. No. 10/896,594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated herein by reference in its entirety.

Figure 3:
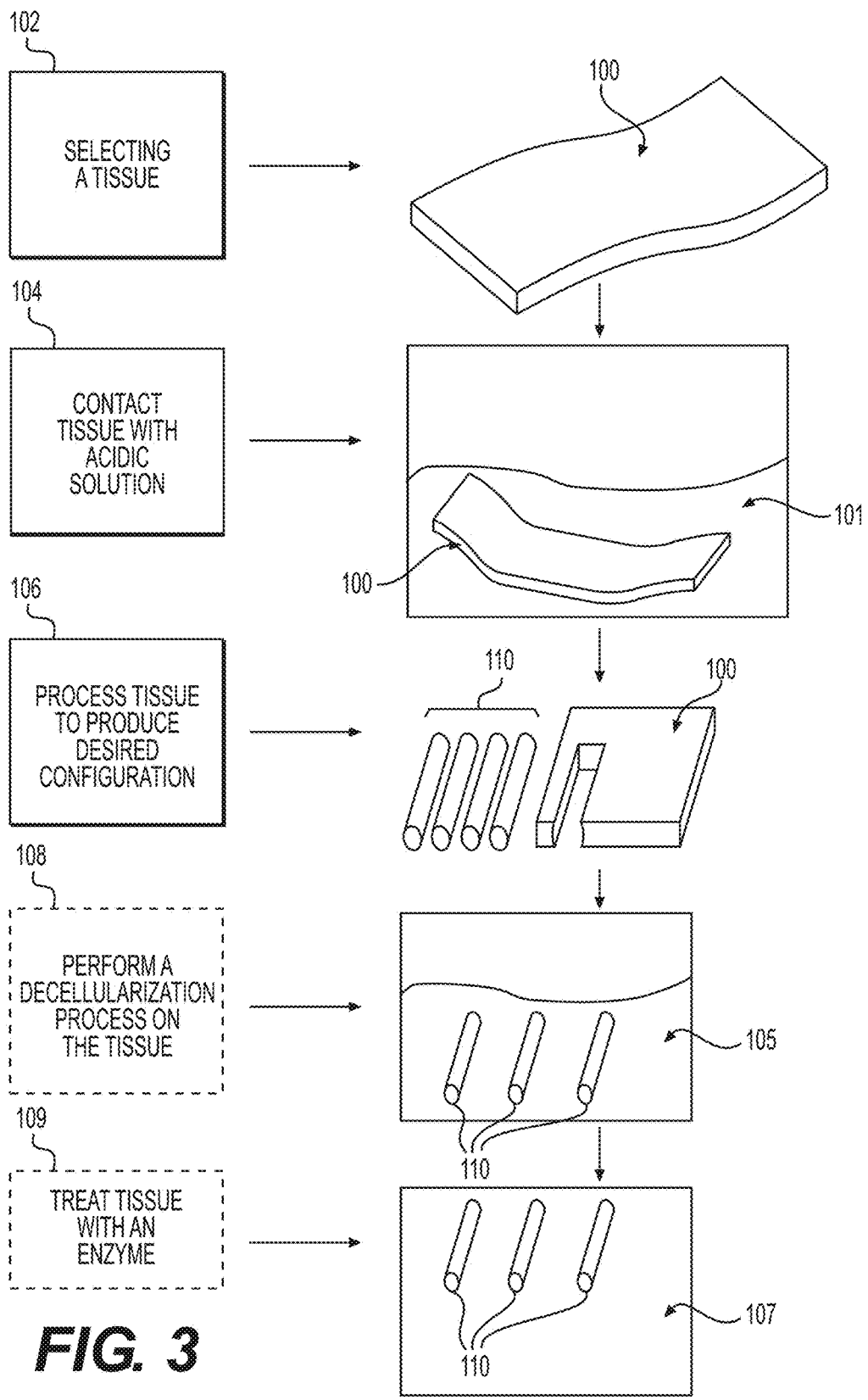
FIG. 3 depicts an alternative process for producing a tissue product according to various embodiments.

In some cases, the tissue can further be treated with one or more enzymes, including proteases. Specifically, Applicant has discovered that treatment of tissues, especially after exposure to conditions such as acidic pH, can improve the biologic response of the tissues when subsequently implanted in the body. FIG. 3, therefore, illustrates an alternative process for producing a wound treatment device 110. The process, as shown, further includes treatment with a protease that can improve the biologic response of the tissue when implanted.

A number of different enzymes can be used to treat the tissue matrices. For example, suitable enzymes can include sulfhydryl proteases such as bromelain. In addition, they can include bromelain, papain, ficin, actinidin, alcalase, trypsin, or combinations thereof. The enzymes can be purchased commercially or extracted from natural sources such as fruit sources or via biologic production.

In certain embodiments, the enzyme is a subtilisin-like serine protease. Various subtilisin-like serine protease activities and treatment times may be used. For example, a subtilisin-like serine protease, such as ALCALASE®, may be provided in a solution at a concentration of about 0.001% to about 0.1% (v/v) with an activity of about $3.0 \times 10^{-5}$ to about $2.0 \times 10^{-3}$ units/mL. In addition, treatment times may vary between about 15 to about 25 hours at ambient (e.g., room) temperature. The activity of a subtilisin-like serine protease, such as ALCALASE®, may be determined by the amount of casein protein that the subtilisin-like serine protease, such as ALCALASE®, can hydrolyze. For example, one unit of a subtilisin-like serine protease, such as ALCALASE®, is the amount of the subtilisin-like serine protease, such as ALCALASE®, that hydrolyzes casein to produce a color equivalent to 1.0 mole of tyrosine per minute at pH 7.5 at 37° C. using a UV spectrophotometer at 280 nm.

The protease can be applied to the tissues in a variety of suitable solutions, at a variety of concentrations, and at a variety of pHs, as described herein. For example, a HEPES buffer comprising ALCALASE® at a concentration of about 0.001% to about 0.1% (v/v) with an activity of about $3.0 \times 10^{-5}$ to about $2.0 \times 10^{-3}$ units/mL and about 5,000 to about 10,000 units/L of a deoxyribonuclease, having a pH of about 7.0 to about 8.0. In some cases, the enzyme can be combined with other processing steps, including for example, along with another enzyme specifically selected to remove alpha-galactose residues, as discussed previously.

In certain embodiments, the enzyme is a trypsin-like serine protease. Various trypsin-like serine protease activities and treatment times may be used. For example, a trypsin-like serine protease, such as trypsin, may be provided in a solution at a concentration of about 0.01 to about 1.0 mg/mL. In addition, treatment times may vary between about 15 to about 25 hours at ambient (e.g., room) temperature.

In certain embodiments, the enzyme is a thiol protease, such as bromelain A, bromelain B, papain, cathepsin K, and calpain. Various thiol protease activities and treatment times may be used. For example, a thiol protease, such as bromelain (bromelain A or B), may be provided in a solution with an activity of about 50 to about 500 units/L, where one unit releases 1.0 μmole of p-nitrophenol from N-α-Z-L-lysine p-nitrophenyl-lysine p-nitrophenyl ester per minute, pH 4.6, at 25° C. In addition, treatment times may vary between about 15 to about 25 hours at ambient (e.g., room) temperature to about 37° C.

Native or engineered, human or non-human dispases suitable for use in the methods herein include those dispases that are neutral proteases that cleave the N-terminal peptide bonds of non-polar amino acid residues, including alanine, valine, leucine, isoleucine, proline, methionine, phenylalanine, and tryptophan.

In certain embodiments, the enzyme is a dispase, such as dispase I. In certain embodiments, the dispase I is a *Bacillus polymyxa* dispase I. Various dispase activities and treatment times may be used. For example, a dispase, such as a dispase I, may be provided in a solution with an activity of about 0.0075 to about 0.75 U/L, where one unit of the dispase I is the amount that hydrolyzes casein to produce a color equivalent to 1.0 mole of tyrosine per minute at pH 7.5 at 37° C. using a UV spectrophotometer at 280 nm. In addition, treatment times may vary between about 15 to about 25 hours at ambient (e.g., room) temperature to about 37° C.

The protease can be applied at various times during processing. For example, in one embodiment, the protease is applied at step 109 in a solution 107 (as shown in FIG. 3) after decellularization. In other embodiments, the enzyme treatment Step 109 is implemented after processing to produce a desired configuration (Step 106), but before decellularization. The protease can be used after acid stiffening to reverse or remove damaged collagen or other altered proteins cause by the acid treatment or other processing steps.

The protease treatment step described as Step 109 can improve the tissue biologic response when the tissue is implanted. For example, without being tied to any particular mechanism of action, the enzyme may improve the biologic response by cleaving or otherwise removing collagen or other proteins in the tissue that are altered by acid processing, or other processing steps. The collagen or other proteins altered by the acid processing may cause an increased inflammatory response as compared to non-acid-treated tissues, and the protease may serve to diminish the inflammatory response. Further, the protease may also improve the biologic response by reducing inflammation associated with native tissue structures and molecules, which may be better removed by protease treatment.

An improved biologic response can be identified using a number of known methods. For example, a change or reduction in inflammation can be ascertained by histologic analysis (e.g., looking for types an presence of inflammatory cells), chemokine measurement, or chemotactic assays. In addition, improved biologic responses, including, improved cellular ingrowth or tissue regeneration, can be ascertained via histologic or gross observations.

Figure 2:
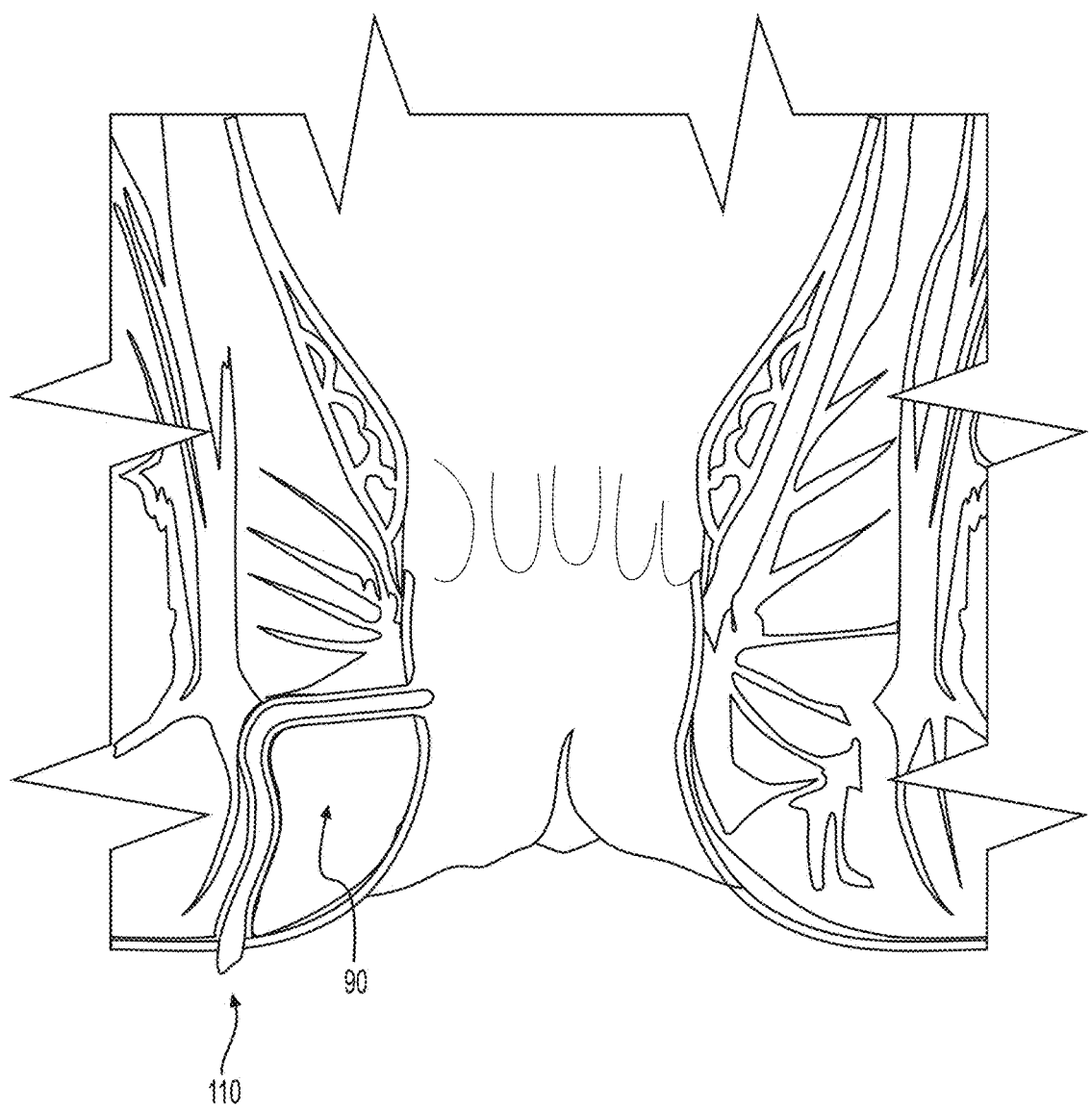
FIG. 2 depicts a method for treating an anal fistula using devices produced by the methods described in the present application.

FIG. 2 illustrates a method for treating an anal fistula 90 using wound treatment devices 110 of the present application. A wound treatment device 110 can be generated by machining a stiffened tissue as described above with reference to FIG. 1. The wound treatment device 110 can be a substantially acellular tissue matrix. The size and shape of the wound treatment device 110 may be chosen such that the device wholly fills the anal fistula 90 without leaving any empty spaces. As shown, the device 110 can be placed into the fistula 90, thereby filling the fistula 90.

The wound treatment device 110 can be produced from a variety of tissue materials, but suitable materials should be compressible such that the material can be passed into a narrow opening and expand to fill a larger or wider area in a fistula or other defects. Accordingly, in some embodiments, the composition of the tissue 100 can include a sponge or similar material. A tissue sponge can include, for example, any tissue matrix material that has been cut or micronized to produce a tissue matrix suspension, and re-suspended to form a sponge-like material.

When implanted in a fistula 90 or other site, the device 110 can be held by natural compressive forces of surrounding tissue. Alternatively, the device 110 can be secured using sutures, clips, staples, surgical adhesives, or other suitable anchoring mechanisms.

Although wound treatment devices are described above in relation to treatment of fistulas or tunneling wounds, it is envisioned that the wound treatment devices of the present disclosure can be used to treat a wide variety of skin wounds. Such wounds and conditions can include (as non-limiting examples) cuts, incisions, abscesses, sacs, ulcers, and/or pustules.

It should be noted that various therapeutic agents can be incorporated into the devices disclosed herein. For example, in various embodiments, the devices can include one or more antimicrobials (antibiotics, antivirals, or antifungals), thrombotic agents, chemotherapeutic agents, or growth factors.

EXAMPLES

For the present examples, porcine acellular dermal matrix plugs (referred to as pADM plugs) in reference to samples made in accordance with the present application, were produced. Porcine hide was procured and subcutaneous fat removed. Dermal tissue was soaked in PBS or in 0.1 M acetic acid, and cylinders were drilled to produce cores of 3 or 5 mm diameter with 3-5 cm length. Cylinders underwent decellularization, and after decellularization were optionally treated with an enzymatic process including ALCALASE® treatment before e-beam sterilization.

Example 1: Analysis of the Effect of Acid Treatment with and without Enzyme (Alcalase Treatment)

Samples of pADM made with acid swelling or PBS soak, and with and without enzyme post processing were implanted in a rat subcutaneous model on the sides of the spine. Accordingly, there were four study groups: (1) pADM made after PBS soak, (2) pADM made with acid stiffening, (3) pADM made after PBS soak with later enzyme treatment, (4) pADM made with acid stiffening and later enzyme treatment.

There were no signs of gross inflammation in any group. All explants were surrounded by vascular connective tissue at two and four weeks. H&E tissue sections were assessed at two and four weeks. The PBS soaked together with enzyme-treated tissue performed best at two and four weeks, as evidenced by cell infiltration, mild inflammation, and moderate vascularization not associated with inflammation. The PBS-soaked and acid-soaked-enzyme-treated group were ranked similarly, with slightly lower cell infiltrate, mild-to-moderate inflammation, and revascularization with inflammation. The acid-soaked tissue without enzyme treatment had the least cell infiltrate, mild to moderate inflammation, and mild revascularization.

Figure 4:
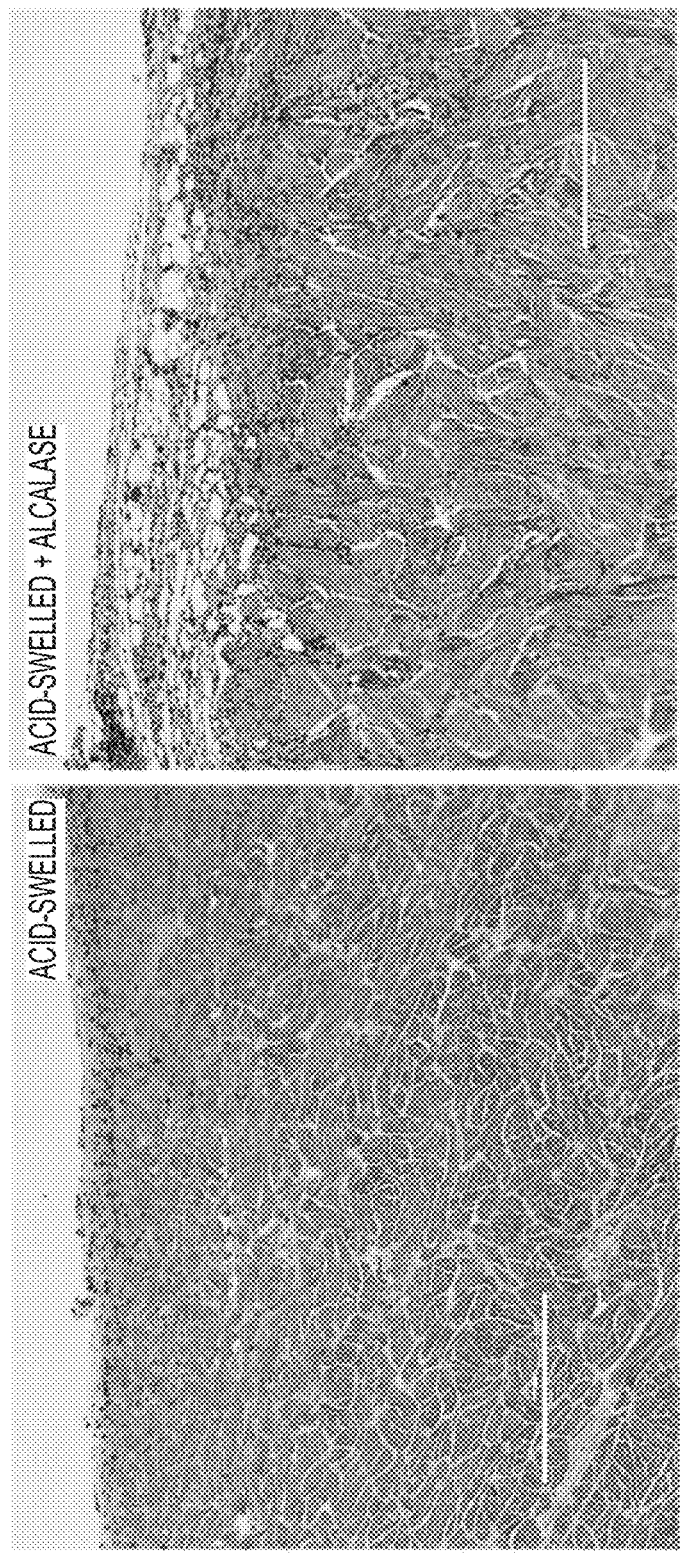
FIG. 4 includes hematoxylin and eosin stained tissue sections from subcutaneous rat implants of tissue processed using acid-stiffening (left) or acid-stiffening following by enzyme treatment, as discussed in Example 1.

FIG. 4 are hematoxylin and eosin stained tissue sections from subcutaneous rat implants of tissue processed using acid-stiffening (left) or acid-stiffening following by enzyme treatment, as discussed herein. Addition of enzyme treatment attenuates the adverse effects of the acid, resulting in lower inflammation levels and higher cell infiltration of fibroblast-like cells.

Figure 5:
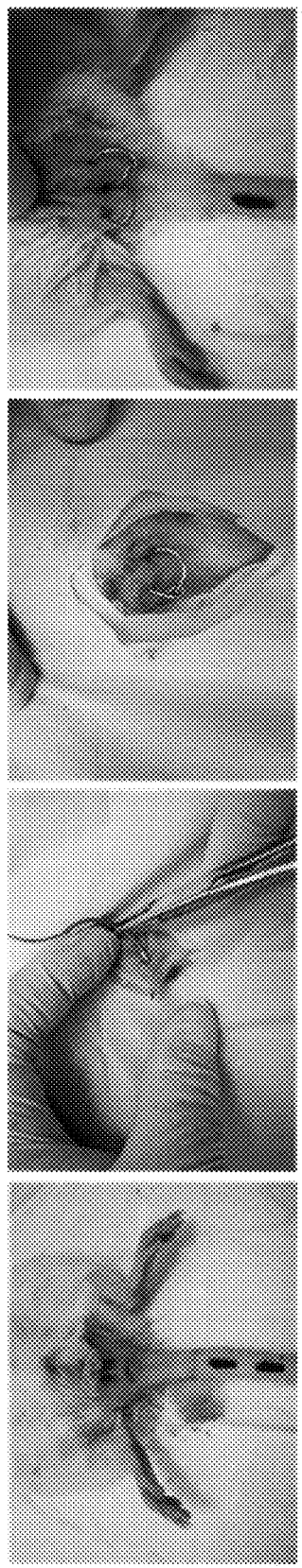
FIG. 5 illustrates a process for production of a mature fistula in a rat, as discussed in Example 2. Acute needle injury is created from the perianal cheek into the anal canal, and a wire suture is put in place for four weeks to allow for creation of a mature fistula-like tract. The wire is removed, light debridement is performed on the tract, and test materials are inserted and sutured in place for testing.

Example 2: Comparison of Fistula Plugs Made with the Present Processes with COOK® BIODESIGN Plugs The present study was designed to assess the biologic response of the present porcine acellular dermal matrix plugs (pADM plugs) and COOK® BIODESIGN anal fistula plugs following creation of a mature, partially re-epithelialized anal fistula-like wound. FIG. 5 illustrates a process for of mature fistula in a rat. Such a procedures is described and adapted from (model adapted from literature: Experimental Model of Anal Fistula in Rats, MS Arakaki et. al., Journal of Coloproctology, 2013; 33(3): 135-138). Acute needle injury is created from the perianal cheek into the anal canal, and a wire suture is put in place for 4 weeks to allow for creation of a mature fistula-like tract. The wire is removed, light debridement is performed on the tract, and test materials are inserted and sutured in place for testing.

Fistula-like wounds were created and developed on each side of the anus in twelve (12) male immune competent rats. At four (4) weeks, one (1) COOK® BIODESIGN plug and one (1) pADM plug were implanted, measuring approximately 2 mm diameter×1 cm long. Animals were euthanized at three (3) and six (6) weeks after implantation. All implants were harvested, placed in cold storage solution, and shipped on wet ice to LIFECELL CORPORATION for histological analysis. All histology samples were cross-sectioned into two (2) pieces, skin and anus side, and individually placed in formalin for H&E, Masson's Trichrome and alpha smooth muscle actin (αSMA) staining.

Slides were blindly assessed by a subject matter expert for: plug persistence, inflammation, vascularity, infection, and level of integration. This scoring became inadequate for comparison amongst groups, due to the lack of COOK® BIODESIGN plugs to assess, even at three weeks.

pADM Plugs: 6/6 plugs persisted to 3-weeks; 5/6 plugs persisted to 6-weeks (by gross visual observation)n. Histological analysis revealed very tight integration with host tissue as early as 3-weeks, even into fat, muscle and loose connective tissue. By 6-weeks, plugs had begun to significantly turnover into new tissue. There were no signs of infection, although inflammation ranged from mild to significant, even at 6-weeks.

COOK® BIODESIGN: 2/6 plugs persisted to 3-weeks; 0/6 plugs were grossly visible at 6-weeks. Histological analysis of the Cook plugs was impossible, due to their eradication by the first study time point. Small pockets of residual inflammation could be seen for 3/6 grafts at 3-weeks, with one case of fistula reformation (re-epithelialization within the tissue); all other samples had been cleared and locally resolved.

Figure 6:
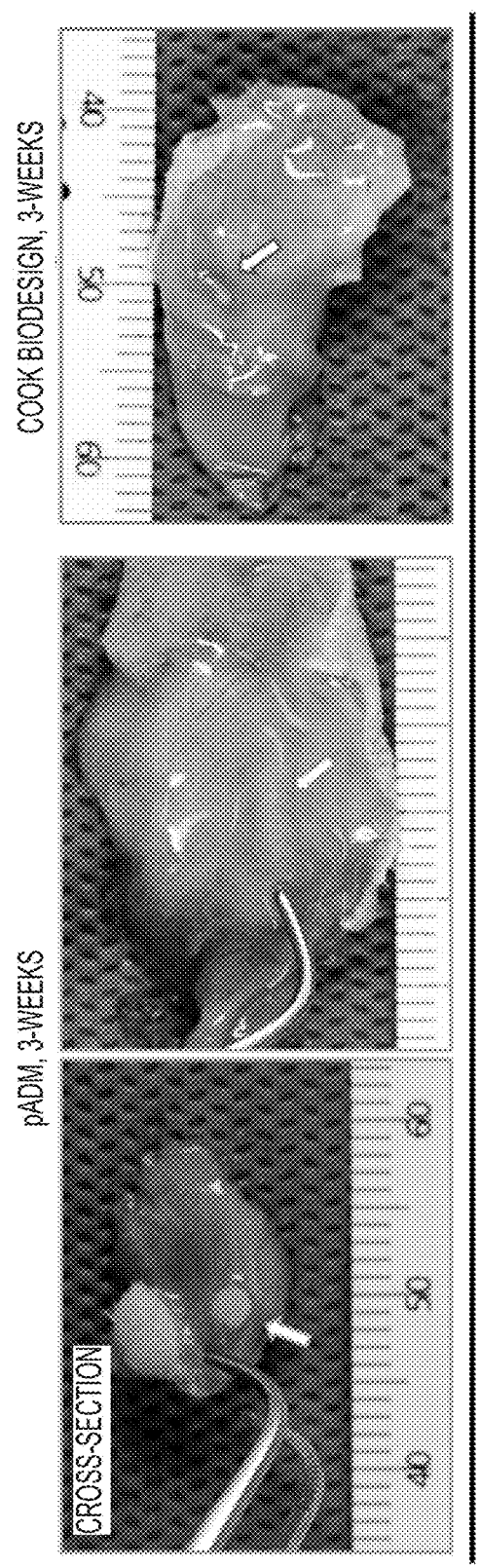
FIG. 6 illustrates gross explants from the anal fistula model discussed in Example 2, including two implant materials produced in accordance with the presently disclosed methods (left two images) and one implant using the COOK® BIODESIGN product.

FIG. 6 illustrates gross explants from the anal fistula model discussed in Example 3, including two implant materials produced in accordance with the presently disclosed methods (left two images) and one implant using the COOK® BIODESIGN product. Gross explants images at 3-weeks of pADM plugs and COOK® BIODESIGN plugs in the anal fistula model. pADM plugs showed drastically better persistence (6/6 plugs were grossly visible, denoted by arrows) and integration compared to Cook plugs (2/6 were slightly palpable, remnants denoted by gray arrow).

Figure 7:
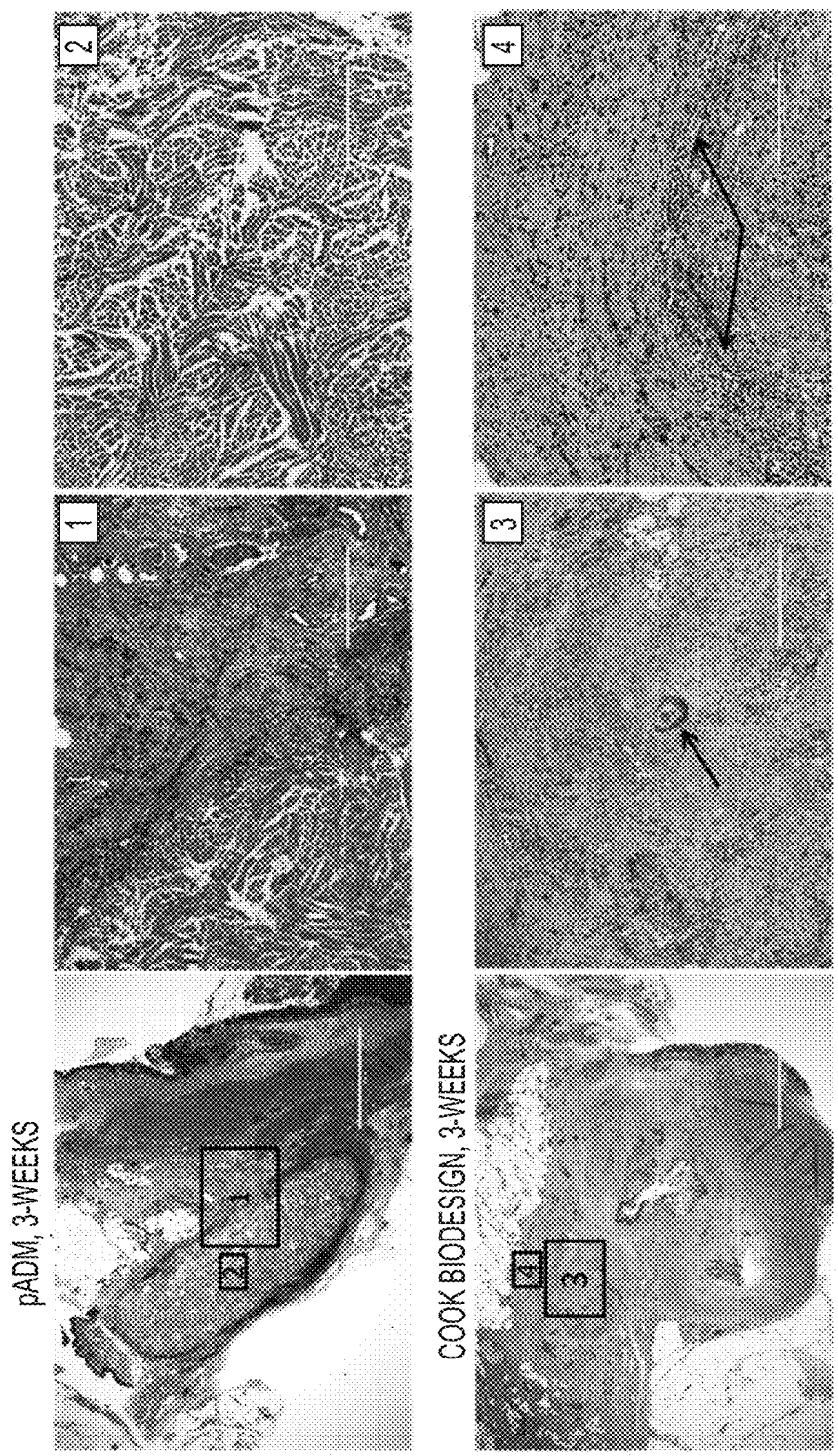
FIG. 7 includes hematoxylin and eosin stained tissue sections from the anal fistula model discussed in Example 2, including materials produced in accordance with the presently disclosed methods (top images) and materials using the COOK® BIODESIGN product.

FIG. 7 are hematoxylin and eosin stained tissue sections from the anal fistula model discussed in Example 3, including materials produced in accordance with the presently disclosed methods (top images) and materials using the COOK® BIODESIGN product. pADM plugs show little-to-no degradation and are well integrated into the surrounding tissue (image 1), with healthy cellular infiltration throughout the plug (image 2). COOK® BIODESIGN plugs are nearly entirely resorbed (image 3), with high levels of residual inflammation at the fibrotic wound interface (image 4, highlighted by double arrows).

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

The invention claimed is:

1. A method of producing a wound treatment device, comprising:
   selecting a tissue;
   contacting the tissue with a solution comprising an acid or a base at a concentration selected to produce a level of stiffness in one or more components in the tissue sufficient to tolerate machining and wherein the solution does not cause substantial irreversible denaturation of one or more components in the tissue; and
   machining the stiffened tissue to produce a desired size and shape.

2. The method of claim 1, wherein the tissue is dermal tissue.

3. The method of claim 1, wherein the tissue is at least one of fascia, pericardial tissue, dura, umbilical cord tissue, cartilage, tendon, reticulate, placental tissue, cardiac valve tissue, ligament tissue, tendon tissue, arterial tissue, venous tissue, neural connective tissue, urinary bladder tissue, ureter tissue, and small-intestine submucosa.

4. The method of claim 1, wherein the one or more components include collagen fibers.

5. The method of claim 1, wherein the solution comprises acetic acid at a concentration of 0.1 M or less.

6. The method of claim 1, wherein the solution has a pH value between 2 and 3.5.

7. The method of claim 1, wherein the step of machining the stiffened tissue comprises machining the stiffened tissue to form an elongated shape.

8. The method of claim 7, wherein the elongated shape is cylindrical and has a length of at least 1 centimeter.

9. The method of claim 7, wherein the elongated shape is cylindrical and has a length of at least 3 centimeters.

10. The method of claim 7, wherein the elongated shape is cylindrical and has a length of at least 5 centimeters.

11. The method of claim 7, wherein the elongated shape is cylindrical and has a diameter in a range of 1 to 5 millimeters.

12. The method of claim 1, further comprising performing a decellularization process on the tissue.

13. The method of claim 12, wherein the decellularization process is performed prior to contacting the tissue with the solution to stiffen the tissue.

14. The method of claim 12, wherein the decellularization process is performed after contacting the tissue with the solution to stiffen the tissue and machining the tissue.

15. The method of claim 1, further comprising treating the tissue with an enzyme.

16. The method of claim 15, wherein the enzyme comprises a subtilisin-like serine protease.

17. The method of claim 15, wherein the enzyme comprises at least one of bromelain, papain, ficin, actinidin, a serine endopeptidase, trypsin, or combinations thereof.

18. The method of claim 15, wherein the enzyme is contacted with the tissue under conditions that result in a tissue having an improved biologic response when implanted in vivo.

19. The method of claim 18, wherein the improved biologic response comprises reduced inflammation as compared to a tissue not treated with the enzyme.

20. The method of claim 18, wherein the improved biologic response comprises improved cellular ingrowth.

\* \* \* \* \*